(12) United States Patent
Yasuda et al.

(10) Patent No.: US 8,846,904 B2
(45) Date of Patent: Sep. 30, 2014

(54) WATER-SOLUBLE PORPHYRIN AND PROCESS FOR PRODUCTION THEREOF

(75) Inventors: Masahide Yasuda, Miyazaki (JP); Tsutomu Shiragami, Miyazaki (JP); Jin Matsumoto, Miyazaki (JP)

(73) Assignee: University of Miyazaki, Miyazaki-shi (JP)

( * ) Notice: Subject to any disclaimer, the term of this patent is extended or adjusted under 35 U.S.C. 154(b) by 84 days.

(21) Appl. No.: 13/500,403

(22) PCT Filed: Oct. 6, 2010

(86) PCT No.: PCT/JP2010/067530
§ 371 (c)(1),
(2), (4) Date: Apr. 5, 2012

(87) PCT Pub. No.: WO2011/043369
PCT Pub. Date: Apr. 14, 2011

(65) Prior Publication Data
US 2012/0202987 A1  Aug. 9, 2012

(30) Foreign Application Priority Data
Oct. 7, 2009 (JP) .................................. 2009-233246

(51) Int. Cl.
C07D 487/22 (2006.01)
C07F 9/6584 (2006.01)
A61K 41/00 (2006.01)
C09B 45/16 (2006.01)
A61K 47/48 (2006.01)
C09B 69/00 (2006.01)

(52) U.S. Cl.
CPC .......... *C07F 9/65846* (2013.01); *C07D 487/22* (2013.01); *A61K 41/0071* (2013.01); *C07F 9/6584* (2013.01); *C09B 45/16* (2013.01); *A61K 47/48215* (2013.01); *C09B 69/00* (2013.01)
USPC ...................................................... 540/145

(58) Field of Classification Search
USPC ...................................................... 540/145
See application file for complete search history.

(56) References Cited

FOREIGN PATENT DOCUMENTS

| | | |
|---|---|---|
| JP | 04-120085 A | 4/1992 |
| JP | 05-247073 A | 9/1993 |
| JP | 06-220343 A | 8/1994 |
| JP | 2004-532890 A | 10/2004 |
| JP | 2008-255011 A | 10/2008 |
| WO | WO-02/098882 A1 | 12/2002 |

OTHER PUBLICATIONS

T. Shimizu et al., "Porphyrin arrays connected with molecular wire," Thin Solid Films, vol. 273, No. 1-2, 1996, pp. 14-19.
P.-C. Cheng et al., "Synthesis and Characterization of Phosphorus Complexes of *MESO*-Tetraphenylporphyrin (tpp), and X-Ray Crystal Structure of [P(tpp)(OCH(CH$_3$)$_2$)$_2$]+Cl$^-$," Polyhedron, vol. 15, No. 16, 1996, pp. 2733-2740.
M. Hartmann et al., "Polymere mit dem Zentralatom eines Makrocyclus in der Hauptkette, 2," Die Makromolekulare Chemie, vol. 176, No. 4, 1975, pp. 831-847.
J. Matsumoto et al., "Water-soluble Porphyrin Easily Derived from Tetraphenylporphyrin: Alkyloxo(methoxo)porphyrinatoantimony Bromides," Chemistry Letters, vol. 37. No. 8, Aug. 5, 2008, pp. 886-887.
M. Yasuda et al., "Visible light-assisted sterilization activity of water-soluble antimonyporphyrin toward *Saccharomyces cerevisiae*," Journal of Photochemistry and Photobiology A: Chemistry, vol. 205, 2009, pp. 210-214.
J. Matsumoto et al., "Water-solubilization of alkyloxo(methoxo)porphyrinatoantimony bromides," Physical Chemistry Chemical Physics, vol. 11, 2009, pp. 9766-9771.
International Search Report dated Jan. 11, 2011, issued for PCT/JP2010/067530.

*Primary Examiner* — Brian McDowell
(74) *Attorney, Agent, or Firm* — Edwards Wildman Palmer LLP; James E. Armstrong, IV

(57) ABSTRACT

The present invention provides a porphyrin derivative having improved water solubility, desirably having both water solubility and lipophilicity. Specifically, the present invention provides a water-soluble porphyrin consisting of a tetraphenylporphyrin derivative represented by Formula (1):

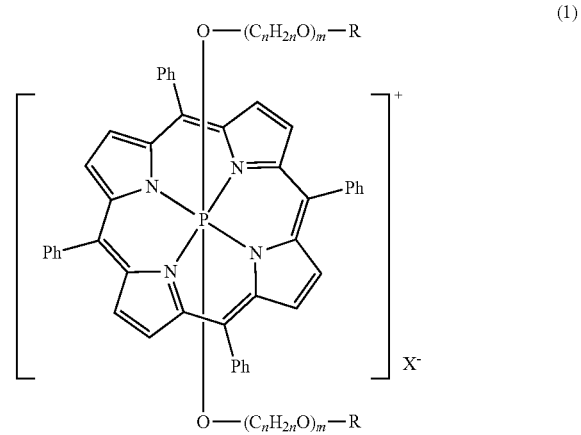

wherein m represents an integer of 1 to 30; n represents an integer of 2 to 4; R represents a hydrogen atom or an optionally substituted alkyl or aromatic group; Ph represents an optionally substituted phenyl group; and X$^-$ is a counterion and represents a halide ion, PF$_6^-$, or BF$_4^-$.

9 Claims, No Drawings

WATER-SOLUBLE PORPHYRIN AND PROCESS FOR PRODUCTION THEREOF

TECHNICAL FIELD

The present invention relates to a water-soluble porphyrin and a process for the production thereof.

BACKGROUND ART

Heretofore, porphyrin derivatives have been used as a photoconductive material, an electrophotographic photoreceptor material, an optical memory material, a photocatalyst material, a material for molecular devices, and the like. For example, Patent Literature 1 and 2 disclose porphyrin derivatives containing various substituents at the ring periphery or as axial ligands. Patent Literature 1 and 2 disclose that these derivatives can be used for the aforementioned purposes.

In recent years, porphyrin derivatives have also been used in fluorescent dyes in the field of biochemistry as well as in photosensitizers for photodynamic therapy (PDT) in the field of medicine. Therefore, improving the water solubility thereof has been a challenge. In relation to this, Patent Literature 3 and 4 disclose porphyrin derivatives having improved water solubility.

For example, Patent Literature 3 discloses water-soluble porphyrin derivatives for use in PDT. According to Patent Literature 3, various substituents are introduced to the periphery of the porphyrin ring so as to improve the water solubility (Claim 19, etc., of Patent Literature 3).

Further, Patent Literature 4 discloses an amphipathic metalloporphyrin complex with cationic hydrophilic groups and lipophilic groups introduced to the ring periphery. Patent Literature 4 further discloses that this complex can be used as a pharmaceutical composition.

Heretofore, porphyrin derivatives having water solubility as described above are known. However, such derivatives are synthesized by introducing a cationic or anionic functional group, or a functional group such as hydrophilic macromolecules, to the periphery of the porphyrin ring, making the synthesis of the derivatives difficult. Further, considering use in the field of biochemistry and use in the field of medicine, porphyrin derivatives are required to have both water solubility and lipophilicity (oil solubility). However, synthesizing a porphyrin derivative that satisfies such a requirement is difficult.

CITATION LIST

Patent Literature

PTL 1: Japanese Unexamined Patent Publication No. H5-247073
PTL 2: Japanese Unexamined Patent Publication No. H6-220343
PTL 3: Japanese Unexamined Patent Publication No. 2004-532890
PTL 4: Japanese Unexamined Patent Publication No. 2008-255011

SUMMARY OF INVENTION

Technical Problem

An object of the present invention is to provide a porphyrin derivative having improved water solubility, desirably having both water solubility and lipophilicity.

Solution to Problem

The present inventors have introduced various axial ligands to a phosphorus tetraphenylporphyrin complex (PTPP) containing phosphorus as the central metal. In terms of the PTPP, since the porphyrin ring itself is a monovalent cation, introduction of ionic groups as substituents is not required. Based on this, the inventors conducted a search of axial ligands that can achieve higher water solubility and higher lipophilicity, by means of a simple process, i.e., performing the conversion of the axial ligands of PTPP. As a result, the inventors found that specific axial ligands can achieve the above object; the present invention was thereby accomplished.

More specifically, the present invention relates to the following water-soluble porphyrin and a process for the production thereof.

1. A water-soluble porphyrin consisting of a tetraphenylporphyrin derivative represented by Formula (1):

$$[\text{structure}]\quad(1)$$

wherein m represents an integer of 1 to 30; n represents an integer of 2 to 4; R represents a hydrogen atom or an optionally substituted alkyl or aromatic group; Ph represents an optionally substituted phenyl group; and $X^-$ is a counterion and represents a halide ion, $PF_6^-$, or $BF_4^-$.

2. The water-soluble porphyrin according to Item 1, wherein the m is an integer of 1 to 9.

3. The water-soluble porphyrin according to Item 1 or 2, wherein the n is an integer of 2 to 3.

4. The water-soluble porphyrin according to any one of Items 1 to 3, wherein the R is methyl, ethyl, butyl, hexyl, dodecyl, or octadecyl.

5. A process for producing the water-soluble porphyrin of Item 1, comprising introducing a ligand having a polyalkylene glycol moiety and a substituent (R) and represented by Formula (2):

$$-\text{O}-(C_nH_{2n}O)_m-R \quad(2)$$

wherein m represents an integer of 1 to 30, n represents an integer of 2 to 4, and R represents a hydrogen atom or an optionally substituted alkyl or aromatic group, to the axial ligand positions of a phosphorus tetraphenylporphyrin complex containing phosphorus as the central metal and serving as a starting material.

6. The water-soluble porphyrin according to any one of Items 1 to 4, which is used as a photosensitizer in photodynamic therapy.

Hereinafter, the water-soluble porphyrin and the process for the production thereof according to the present invention are described in detail.

Water-soluble Porphyrin

One of the features of the water-soluble porphyrin of the present invention is that it consists of a tetraphenylporphyrin derivative represented by Formula (1) above.

The water-soluble porphyrin of the present invention having such a feature is based on a cationic phosphorus tetraphenylporphyrin complex (PTPP) in which phosphorus (P) is incorporated into tetraphenylporphyrin ($H_2TPP$) as the central metal, and a ligand having a polyalkylene glycol moiety and a substituent (R) and represented by Formula (2) above is introducing to the axial ligand positions.

The Ph above represents an optionally substituted phenyl group. Examples of substituents of phenyl include $C_{1-20}$ alkyl, $C_{1-20}$ alkoxy, halogens such as chlorine, bromine, fluorine, and iodine, and nitro.

The m in the above-described ligand is the number of alkylene glycol moieties, and may be an integer of 1 to 30, preferably 1 to 9. When the m is 1 or more, the water solubility of PTPP can be improved to 1 mM or more.

The n in the above-described ligand may be an integer of 2 to 4, and preferably 2 to 3. The alkylene glycol represented by $(C_nH_{2n}O)$ is preferably ethylene glycol or propylene glycol. A compound having one or more alkylene glycol moieties and a substituent (R) is commonly used as a nonionic surfactant, and helps to improve the water-solubility of PTPP.

The R in the above-described ligand represents a hydrogen atom or an optionally substituted alkyl or aromatic group, each of which imparts lipophilicity to PTPP. When the R is alkyl, the number of carbon atoms is preferably about 1 to 20 in consideration of the handling thereof. Alkyl groups having any number of carbon atoms can achieve the solubility of 0.1 mM or more (solvent: dioxane). Examples of alkyl groups include methyl, ethyl, butyl, hexyl, decyl, dodecyl, tetradecyl, hexadecyl, octadecyl, and the like. Of these, methyl, ethyl, butyl, hexyl, dodecyl, and octadecyl are particularly preferable.

The water solubility tends to decrease as the number of carbon atoms of alkyl increases. Therefore, when an alkyl group having a large number of carbon atoms is attached, by increasing the m representing the alkylene glycol moieties, the water solubility can be ensured.

The $X^-$ above is a counterion and represents a halide ion, $PF_6^-$, or $BF_4^-$. Examples of halide ions include $Cl^-$, $Br^-$, $I^-$, and the like.

The above-described water-soluble porphyrin of the present invention has not only water solubility but also lipophilicity, and thus has high biocompatibility with microorganisms, cells, and the like. For this reason, the water-soluble porphyrin of the present invention can be suitably used as a fluorescent dye in the field of biochemistry or as a photosensitizer in the field of medicine (for PDT use).

The PDT mentioned above is a therapy that treats diseases, such as malignant tumors and rheumatic gout, by administering a photosensitizer such as a porphyrin to a patient, and thereafter, irradiating only a treatment site with light to selectively activate the photosensitizer only at the treatment site. When used as a photosensitizer for PDT, the water-soluble porphyrin of the present invention may be mixed with a pharmacologically acceptable carrier, an excipient, a diluent, and the like, and may ordinarily be used in the form of an injection. When PDT treatment is performed, an injection containing the water-soluble porphyrin is administered to a treatment site, and the treatment site is then irradiated with light to activate the porphyrin. Thereby, the ambient oxygen molecules undergo light excitation and are converted to singlet oxygen having strong oxidizability (Singlet Oxygen: $^1O_2$). The $^1O_2$ oxidizes the treatment site and can thereby destroy the lesion. As the light used for irradiation, light having a wavelength and intensity sufficient to activate porphyrin may be selected. The light irradiation may be performed using, for example, an optical fiber inserted in a catheter, if necessary.

Process for the Production of Water-Soluble Porphyrin

The process for producing water-soluble porphyrin of the present invention is not limited. Examples of preferable processes include a process comprising introducing a ligand represented by Formula (2) above to the axial ligand positions of a phosphorus tetraphenylporphyrin complex containing phosphorus as the central metal and serving as a starting material (hereinafter referred to as "the production process of the present invention"). The following describes the above.

As a starting material, a dichloro complex represented by Formula (3) below is particularly preferable. A dichloro complex can be synthesized by subjecting, for example, tetraphenylporphyrin (with the proviso that the phenyl is optionally substituted) to a reaction with $POCl_3$.

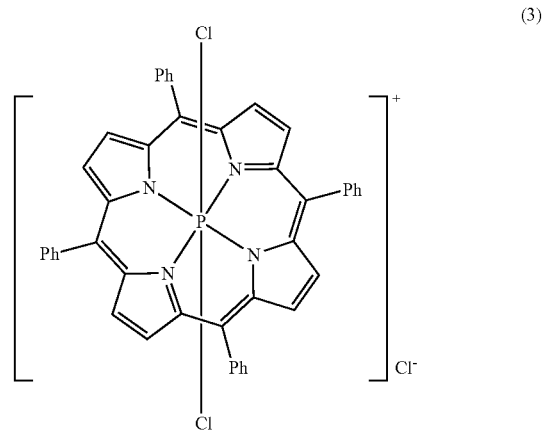

(3)

Subsequently, a ligand represented by Formula (2) is introduced thereto by reacting the complex of Formula (3) with a compound having a polyalkylene glycol moiety and a substituent (R) and represented by Formula (4):

HO—$(C_nH_{2n}O)_m$—R  (4)

wherein m represents an integer of 1 to 30; n represents an integer of 2 to 4; and R represents a hydrogen atom or an optionally substituted alkyl or aromatic group.

By performing the above-described reaction in a solvent, such as acetonitrile, while heating under reflux for several hours, the ligand can be easily introduced.

In a case where a compound represented by Formula (4) above is not easily obtained, the complex represented by Formula (3) can be reacted with polyalkylene glycol, followed by a reaction with alkyl halide, acid chloride, a benzyl halide derivative, and the like. Thereby, a tetraphenylporphyrin derivative represented by Formula (1) above can also be synthesized.

The counterion ($X^-$) of PTPP may be selected from a halide ion, $PF_6^-$, or $BF_4^-$. Examples of halide ions include $Cl^-$, $Br^-$, $I^-$, and the like.

Advantageous Effects of Invention

The water-soluble porphyrin of the present invention is based on a PTPP complex in which phosphorus is incorporated into $H_2TPP$ as the central metal, and a ligand represented by Formula (2) is introduced to the axial ligand positions.

In the present invention, a ligand represented by Formula (2) is introduced to the axial ligand positions, using a simple synthetic method, and water solubility as well as lipophilicity can thereby be imparted to the porphyrin derivative. Therefore, the porphyrin derivative of the present invention has high biocompatibility with microorganisms, cells, and the like, and can thus be suitably used as a fluorescent dye in the field of biochemistry or as a photosensitizer in the field of medicine (for PDT use).

DESCRIPTION OF EMBODIMENTS

Hereinafter, the present invention is described in further detail with reference to Examples and Comparative Examples. However, the present invention is not limited to the Examples.

EXAMPLE 1

75 mg of the complex represented by Formula (3) and 10 mL of the compound represented by Formula (4) (with the proviso that m=3, n=2, and R is methyl) were dissolved in 20 mL of acetonitrile.

Thereafter, several drops of pyridine were added thereto, and the resulting product was heated under reflux for several hours. The reaction solution was concentrated, and then dissolved in chloroform while being washed with water. Subsequently, the organic layer was concentrated, followed by reprecipitation using hexane.

The crude reaction product was purified by column chromatography on silica gel as a carrier using an eluent of chloroform-methanol, where the ratio was gradually changed from 100:1 to 30:1.

Thereby, the PTPP derivative represented by Formula (1) (with the proviso that m=3, n=2, and R is methyl) was obtained in an amount of 67 mg (yield: 67%).

The analytical data of the obtained PTPP derivative are shown below.

$^1H$ NMR (400 MHz, $CDCl_3$) δ=−2.25 (dt, J=11.9, 5.7 Hz, 4H), 0.57 (td, J=5.7, 1.5 Hz, 4H), 2.19-2.21 (m, 4H), 2.71-2.74 (m, 4H), 3.04-3.06 (m, 4H), 3.15 (s, 6H), 3.15-3.17 (m, 4H), 7.75-7.82 (m, 12H), 7.96-7.98 (m, 4H), 9.06 (d, J=3.0 Hz, 8H); UV-vis (in MeOH) $\lambda_{max}$/nm ($\epsilon$/$10^4$ $M^{-1}$ $cm^{-1}$) 429 (28.6), 560 (1.35), 601 (0.38); Exact mass. Calcd. for $C_{58}H_{58}N_4O_8P$ [$M^+$]: 969.3992. Found: 969.4018.

10 mg of the obtained PTPP derivative was dispersed in 0.50 mL of water and allowed to stand for 3 days to prepare a saturated aqueous solution. The supernatant of the aqueous solution was collected and diluted with methanol. Thereafter, the absorption spectrum was measured and the solubility in water (Cw) was calculated using the molar absorption coefficient of the PTPP derivative in methanol. In a similar manner to the above, the solubility in dioxane (Co) was also calculated.

A water-immiscible organic solvent, such as octanol or chloroform, was added to the aqueous solution of the PTPP derivative (Cw=17.3 mM, Co=0.245 mM) and stirred. This caused the PTPP derivative dissolved in the aqueous phase to promptly move to the organic phase. It is thereby demonstrated that the PTPP derivative has high partition coefficient to the organic phase.

Subsequently, the biocompatibility of this PTPP derivative was assessed in the following manner. An aqueous solution of this PTPP derivative (0.5 mL, 50 μm) was added to the cell suspension (1.0 mL; ca. $2.5 \times 10^4$ cell/mL) of yeast, and then an aqueous solution of agar (1 wt %; 1.0 mL) was added. A portion of the prepared aqueous solution containing the PTPP derivative (10 μm), yeast (*Saccharomyces cerevisiae*; ca. $1.0 \times 10^4$ cell/mL) and agar (0.4 wt %) was placed on a space (1 cm×1 cm) surrounded by a silicone spacer (thickness 50 μm) put on a glass slide, covered with a cover glass. The glass slide was set on the stage of an optical microscope. Thereafter, appropriate bacterial cells were positioned in the center of the field of view, and the Q-band absorption spectrum of the PTPP derivative near 560 nm was measured. Then, the concentration (Cad) of the PTPP derivative adsorbed on the bacterial cells was calculated from absorption spectrophotometry based on the Lambert-Beer law. Table 1 shows the measurement results of Cw, Co, and Cad.

EXAMPLES 2 TO 9 AND COMPARATIVE EXAMPLES 1 AND 2

PTPP derivatives were synthesized as in Example 1, except that the m, n, and R of the compound represented by Formula (4) were changed as shown in Table 1, and the solubility values Cw and Co, and Cad were calculated (Table 1).

TABLE 1

|  | m | n | R | Solubility[a]/mM Cw | Solubility[a]/mM Co | Cad[b]/mM |
|---|---|---|---|---|---|---|
| Example 1 | 3 | 2 | Methyl | 17.3 | 0.245 | Nd[c] |
| Example 2 | 2 | 2 | Methyl | 13.9 | 0.140 | 17.8 |
| Example 3 | 2 | 2 | Ethyl | 13.0 | 0.169 | 27.5 |
| Example 4 | 2 | 2 | Butyl | 5.38 | 0.293 | 74.6 |
| Example 5 | 2 | 2 | Hexyl | 2.07 | 0.244 | 146 |
| Example 6 | 1 | 2 | Hexyl | 1.11 | 0.242 | 142 |
| Example 7 | 9 | 2 | Dodecyl | 14.46 | ≥25 |  |
| Example 8 | 4 | 2 | Octadecyl | 7.96 | ≥25 |  |
| Example 9 | 12 | 3 | Butyl | 2.02 | ≥25 |  |
| Comp. Example 1 | 0 | — | Hexyl | 0.0226 | 0.178 |  |
| Comp. Example 2 | 0 | — | Decyl | 0.0232 | 0.237 |  | a) Cw: solubility in water; Co: solubility in dioxane
b) Cad: concentration of PTPP derivative adsorbed on bacterial cell when 10 μM of PTPP derivative was added to a yeast solution ($1.0 \times 10^4$ cell/mL)
c) Nd: below the detection limit As is clear from the results shown in Table 1, when the m is 1 or more, the solubility in water (Cw) can be improved to 1 mM or more. Additionally, when the R is methyl, ethyl, butyl, hexyl, dodecyl, or octadecyl, the solubility in dioxane (Co) can be improved to 0.1 mM or more. Although the lower limit of the Cad cannot particularly be determined for use as an index of the biocompatibility that achieves PDT efficacy, the lower limit of the Cad is about 10 mM.

When the photosensitizer "Photofrin" that has been practically used in PDT treatment is used, the quantum yield of $^1O_2$ is 0.53 (J. Photochem. Photobiol. B, 92 (2008), 59-65). In contrast, when the PTPP derivatives prepared in Examples 2, 3, and 4 were used, the quantum yields of $^1O_2$ were 0.62, 0.69, and 0.73, respectively. This explains that the water-soluble porphyrins of the present invention have high photoexcitation efficiency and can thus be suitably used for PDT. The quantum yields of the $^1O_2$ production were determined by directly measuring the near infrared emission near 1,270 nm obtained by deactivation of the produced $^1O_2$.

Specifically, an aqueous PTPP derivative solution (20 μM) was irradiated with a laser beam of 558 nm to excite the PTPP derivative, and the emission spectrum of the produced $^1O_2$ was measured. The quantum yield of the $^1O_2$ production was calculated by comparing the emission intensity at 1,270 nm obtained with respect to the aqueous PTPP derivative solution with the emission intensity at 1,270 nm obtained in the same manner as above with respect to methylene blue (quantum yield: 0.52).

The invention claimed is:

1. A water-soluble porphyrin consisting of a tetraphenylporphyrin derivative represented by Formula (1):

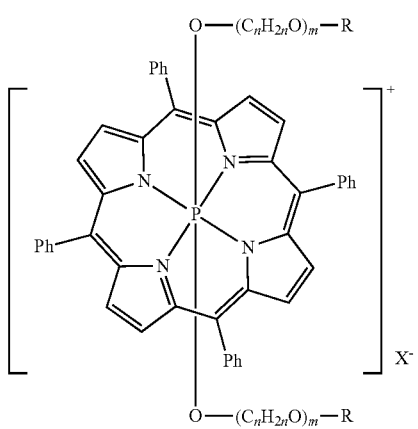

wherein m represents an integer of 1 to 30; n represents an integer of 2 to 4; R represents an alkyl group; Ph represents an optionally substituted phenyl group; and $X^-$ is a counterion and represents a halide ion, $PF_6^-$, or $BF_4^-$.

2. The water-soluble porphyrin according to claim 1, wherein the m is an integer of 1 to 9.

3. The water-soluble porphyrin according to claim 1, wherein the n is an integer of 2 to 3.

4. The water-soluble porphyrin according to claim 1, wherein the R is methyl, ethyl, butyl, hexyl, dodecyl, or octadecyl.

5. A process for producing the water-soluble porphyrin of claim 1, comprising introducing a ligand having a polyalkylene glycol moiety and a substituent (R) and represented by Formula (2):

$$—O—(C_nH_{2n}O)_m—R \quad (2)$$

wherein m represents an integer of 1 to 30, n represents an integer of 2 to 4, and R represents an alkyl group, to the axial ligand positions of a phosphorus tetraphenylporphyrin complex containing phosphorus as the central metal and serving as a starting material.

6. The water-soluble porphyrin according to claim 2, wherein the n is an integer of 2 to 3.

7. The water-soluble porphyrin according to claim 2, wherein the R is methyl, ethyl, butyl, hexyl, dodecyl, or octadecyl.

8. The water-soluble porphyrin according to claim 3, wherein the R is methyl, ethyl, butyl, hexyl, dodecyl, or octadecyl.

9. The water-soluble porphyrin according to claim 6, wherein the R is methyl, ethyl, butyl, hexyl, dodecyl, or octadecyl.

* * * * *